(12) United States Patent
Haziza

(10) Patent No.: US 11,278,326 B2
(45) Date of Patent: Mar. 22, 2022

(54) FLEXIBLE SPINAL FUSION ROD

(71) Applicant: Premia Spine Ltd., Ramat Poleg (IL)

(72) Inventor: Rafi Haziza, Kiryat Bialik (IL)

(73) Assignee: Premia Spine Ltd., Ramat Poleg (IL)

( * ) Notice: Subject to any disclaimer, the term of this patent is extended or adjusted under 35 U.S.C. 154(b) by 130 days.

(21) Appl. No.: 16/578,521

(22) Filed: Sep. 23, 2019

(65) Prior Publication Data

US 2021/0085371 A1 Mar. 25, 2021

(51) Int. Cl.
| | |
|---|---|
| *A61B 17/70* | (2006.01) |
| *A61B 17/84* | (2006.01) |
| *A61F 2/30* | (2006.01) |
| *A61F 2/44* | (2006.01) |

(52) U.S. Cl.
CPC ...... *A61B 17/7013* (2013.01); *A61B 17/7019* (2013.01); *A61B 17/84* (2013.01); *A61F 2002/30738* (2013.01); *A61F 2002/4415* (2013.01); *A61F 2310/00023* (2013.01)

(58) Field of Classification Search
CPC . A61B 17/7013; A61B 17/7019; A61B 17/84; A61B 17/866; A61B 17/8605; A61B 17/864; A61B 17/869; A61B 17/7208; A61B 17/8625; A61B 17/7233; A61B 17/7029; A61B 17/7001; A61B 17/7023; A61B 17/7031; A61B 17/7041; A61F 2/44; A61F 2002/30738; A61F 2002/4415; A61F 2002/3055; A61F 2002/30405; A61F 2002/30563; A61F 2002/30566; A61F 2002/30649; A61F 2002/30841; A61F 2310/00023
See application file for complete search history.

(56) References Cited

U.S. PATENT DOCUMENTS

| | | | | |
|---|---|---|---|---|
| 7,621,612 | B2 * | 11/2009 | Yamaguchi | B41J 2/14153 347/17 |
| 7,621,912 | B2 * | 11/2009 | Harms | A61B 17/645 606/246 |
| 7,766,942 | B2 * | 8/2010 | Patterson | A61B 17/7011 606/261 |
| 8,376,865 | B2 * | 2/2013 | Forster | A61M 25/0113 464/78 |
| 9,579,132 | B2 * | 2/2017 | Krause | A61B 17/864 |
| 2008/0312694 | A1 | 12/2008 | Peterman | |
| 2013/0103091 | A1 * | 4/2013 | Acosta, Jr | A61B 17/7013 606/259 |

FOREIGN PATENT DOCUMENTS

| | | |
|---|---|---|
| FR | 2715825 | 8/1995 |
| KR | 20110094890 | 8/2011 |
| WO | 2005/039454 | 5/2005 |
| WO | 2007/123920 | 11/2007 |
| WO | 2014/011939 | 1/2014 |

OTHER PUBLICATIONS

PCT Search Report and Written Opinion PCT/IB2020/058776, dated Jan. 29, 2021.

* cited by examiner

*Primary Examiner* — Pedro Philogene
(74) *Attorney, Agent, or Firm* — Dekel Patent Ltd.; David Klein

(57) ABSTRACT

A spinal rod assembly includes a flexible spinal fusion rod including link members that articulate with one another so that the rod is formable into a curved orientation. A locking mechanism is coupled to the link members and can lock the link members so that the rod is maintained in the curved orientation.

8 Claims, 4 Drawing Sheets

FLEXIBLE SPINAL FUSION ROD

FIELD OF THE INVENTION

The present invention relates generally to spinal fusion rods, and particularly to a flexible spinal fusion rod.

BACKGROUND OF THE INVENTION

Degenerative spinal column diseases, such as disc degenerative diseases, spinal stenosis, spondylolisthesis, and others, are typically treated by spinal decompression. The primary purpose of decompression is to reduce pressure in the spinal canal and on nerve roots by removing a certain tissue of the spinal column to reduce or eliminate the pressure and pain caused by the pressure. If the tissue of the spinal column is removed the pain is reduced but the spinal column is weakened. Therefore, fusion surgery is often necessary for spinal stability following the decompression procedure.

Spinal fusion is a procedure that involves joining two or more adjacent vertebrae with a bone fixation device so that they no longer are able to move relative to each other. Spinal fixation devices typically include a spinal fixation element, such as a relatively rigid fixation rod, that is coupled to adjacent vertebrae by attaching the element to various anchoring devices, such as hooks, bolts, wires, or screws.

SUMMARY OF THE INVENTION

The present invention seeks to provide an improved flexible spinal fusion rod, as is described more in detail hereinbelow. The invention allows the rod to be flexible during the insertion process (e.g., insertion in the tulip heads of pedicle screws).

There is thus provided in accordance with an embodiment of the present invention a spinal rod assembly including a flexible spinal fusion rod including link members that articulate with one another so that the rod is formable into a curved orientation, and a locking mechanism coupled to the link members and configured to lock the link members so that the rod is maintained in the curved orientation.

The locking mechanism may include a flexible elongate member that passes through lumens of the link members from one portion to another portion of the rod, and a fastener arranged to presses the flexible elongate member against an inner wall of at least one of the lumens to lock the flexible elongate member in place.

The flexible elongate member may pass through lumens of the link members from one end to another end of the rod.

The rod may include at least one chamfered end.

Each of the link members may include a male tenon that protrudes from a body portion and which is received in a female mortise of an adjacent link member.

The male tenon may include a distal convex portion which extends laterally on opposite sides of a longitudinal axis of the rod to lateral convex portions. The male tenon may taper proximally from each of the lateral convex portions to inflection points located on opposite sides of the longitudinal axis. The male tenon may gradually narrow to a narrowest point on a concave path on opposite sides of the longitudinal axis. The male tenon may gradually widen in a concave shape to the body portion. The female mortise may be shaped to complement shapes of the distal convex portion, the lateral convex portions, the concave path and the concave shape of the male tenon.

A gap may be between an outer edge of each of the lateral convex portions and an adjacent inner wall of each of the female mortises.

The rod may include one or more markers. The rod may include a cover.

BRIEF DESCRIPTION OF THE DRAWINGS

The present invention will be understood and appreciated more fully from the following detailed description, taken in conjunction with the drawing in which.

DETAILED DESCRIPTION OF EMBODIMENTS

Figure 1:
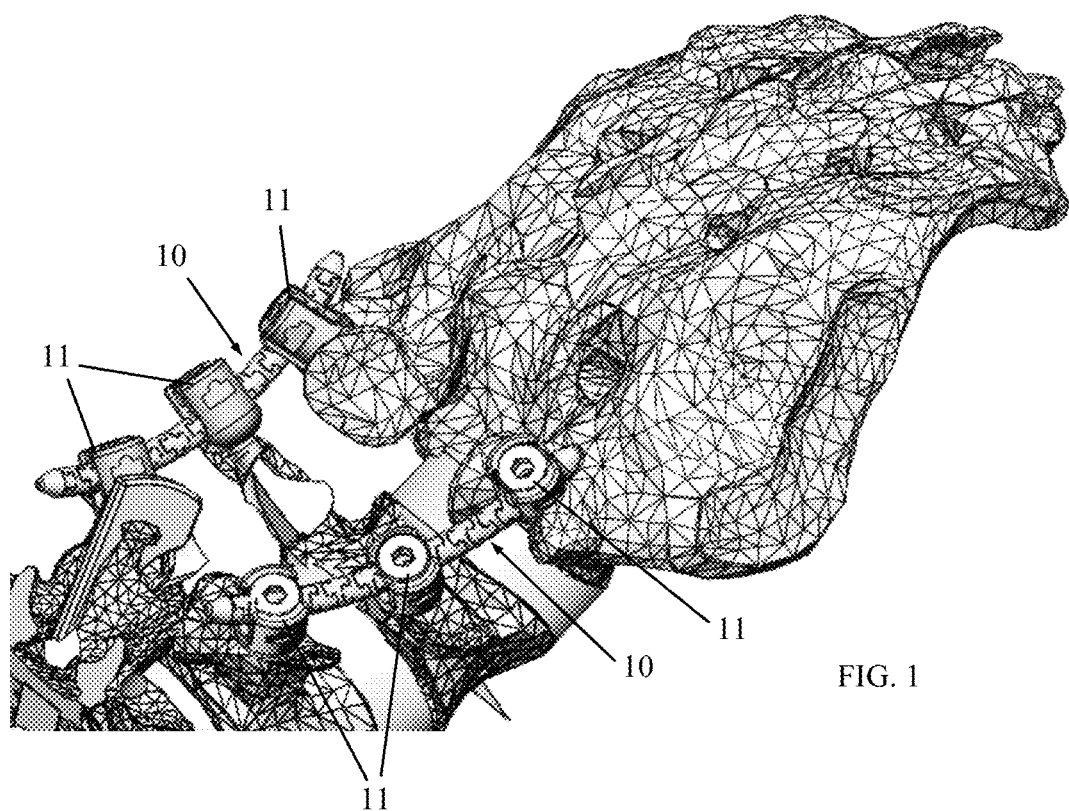
FIG. 1 is a simplified pictorial illustration of a flexible spinal fusion rod installed on pedicle screws on vertebrae of a patient, in accordance with a non-limiting embodiment of the present invention.

Reference is now made to FIG. 1, which illustrates a flexible spinal fusion rod 10 installed on pedicle screws 11 on vertebrae of a patient, in accordance with a non-limiting embodiment of the present invention. In FIG. 1, two such rods 10 are installed in the patient (left and right rods). The flexible rod 10 may be installed in a minimally-invasive surgical (MIS) procedure and may be used in a fixation procedure, for example, in the lumbar and sacral region (e.g., L3-S1 region).

In one aspect, the flexible rod 10 is capable of articulating. The rod may be fixed to two or more pedicle screws 11 and remains non-rigid. The rod 10 has link members that allow it to have variability flexibility depending on the direction of the movement. For example, rod 10 can have more flexion than extension. The rod and rods can be varied to have identical or variable bending, identical or variable left versus right bending, and identical or variable left and right rotation. The flexibility of the rod enables easy installment of the rod from one screw to another in single- or multi-level fusions. This solves the problem of aligning the rod even in situations where the screws are not necessarily aligned due to patient anatomy.

In another aspect, as will be described below, rod 10 can be locked at any desired straight or curved orientation.

Figure 2:
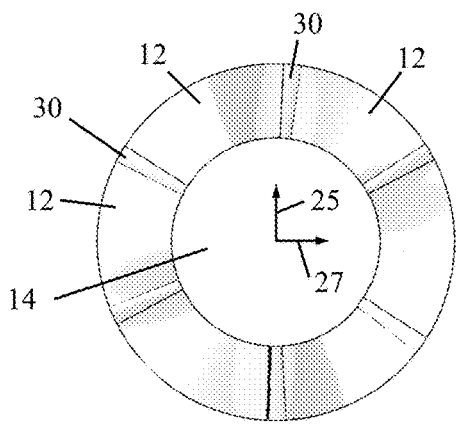
FIG. 2 is an end view of the flexible spinal fusion rod.
Figure 3:
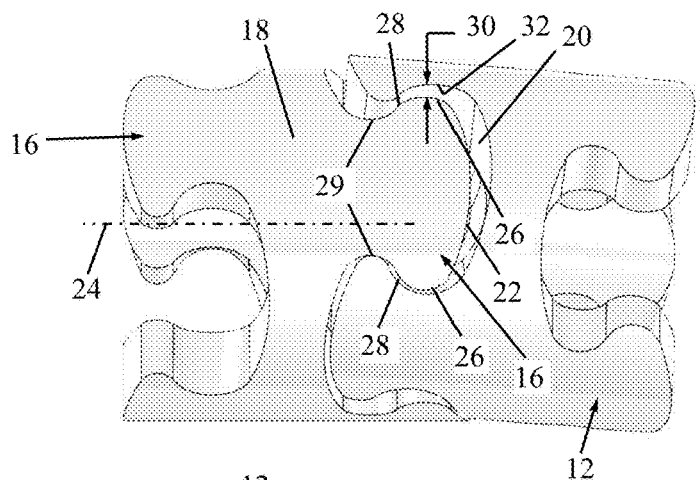
FIG. 3 is an enlarged illustration of two link members of the flexible spinal fusion rod.

Reference is now made to FIGS. 2-3, which illustrate the structure of the flexible spinal fusion rod 10. Rod 10 includes interlocking link members 12 made of a surgically safe material, such as but not limited to, cobalt-chromium alloys, stainless steel alloys, titanium alloys or polymers. In the illustrated embodiment, the link members 12 have a round (circular) periphery but can have other shapes as well. Each link member 12 has an inner lumen 14. Adjacent link members 12 are coupled to each other by means of male and female jigsaw puzzle connections.

Accordingly, as seen in FIG. 3, each link member 12 includes a male tenon 16 that protrudes from a body portion 18 and which is received in a female mortise 20 of an adjacent link member 12. The male tenon 16 includes a distal convex portion 22 (distal meaning away from body portion 18 along a longitudinal axis 24 of the rod 10) which extends laterally on opposite sides of the longitudinal axis 24 to lateral convex portions 26. The male tenon 16 tapers proximally (that is, towards body portion 18) from each of the lateral convex portions 26 to inflection points 28 located on opposite sides of the longitudinal axis 24. Inflection point means the curvature changes from convex to concave. The male tenon 16 then gradually narrows to a narrowest point 29 on the concave path on opposite sides of the longitudinal axis 24. The male tenon 16 then gradually widens in a concave shape to the body portion 18. The male tenon 16 is thus narrower at the inflection points 28 than at the lateral convex portions 26 but the inflection points are not at the narrowest width of the tenon. The radius of curvature of the distal convex portion 22 is not necessarily the same as (and may typically be larger than) the radius of curvature of the lateral convex portions 26. The female mortise 20 is shaped to complement the shape of the male tenon 16 (that is the "negative" of the male tenon shape).

There is a gap 30 between the outer edge of each lateral convex portion 26 and an adjacent inner wall 32 of mortise 20. The size of gap 30 determines the amount of axial rotation of the link members with respect to each other (that is, bending or rotation about an axis 25 or axis 27 in FIG. 2, both of which are perpendicular to the longitudinal axis 24; axis 24 is perpendicular to the drawing sheet in FIG. 2). The size of gap 30 also determines the amount of lateral or longitudinal linear motion of the link members with respect to each other. The size of gap 30 can be selected to control the range of motion of each degree of freedom. In biomechanical terms, this degree of freedom allows spine movement of flexion and extension.

Figure 4:
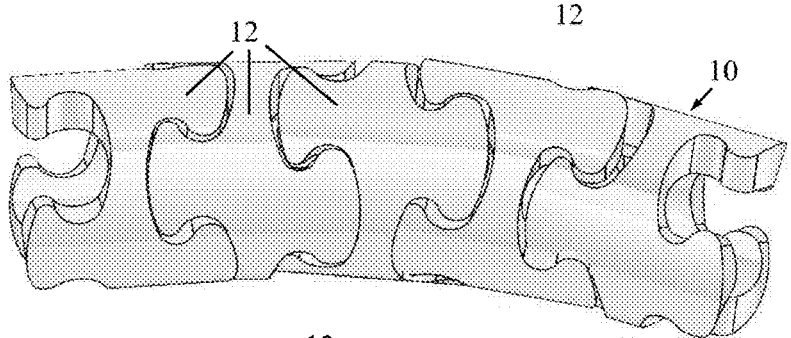
FIG. 4 is a simplified pictorial illustration of more link members of the flexible spinal fusion rod with the rod in a curved, bent orientation.

Reference is now made to FIG. 4, which illustrates link members 12 of the flexible spinal fusion rod 10 in a curved, bent orientation.

Figure 5:
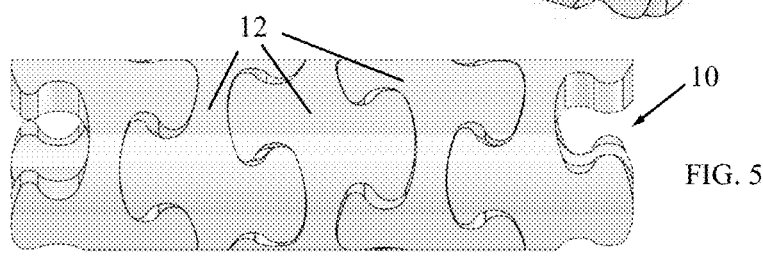
FIGS. 5 and 6 are simplified pictorial illustrations of the flexible spinal fusion rod in respective contracted and expanded linear orientations.
Figure 6:
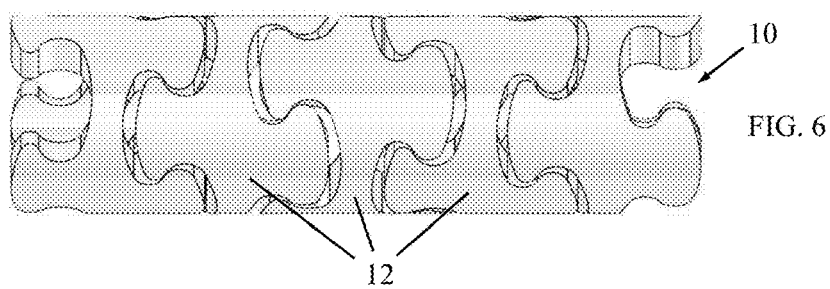

Reference is now made to FIGS. 5 and 6. In FIG. 5, the link members 12 of fusion rod 10 are in a contracted orientation; in FIG. 6, they are in an expanded linear orientation.

Figure 7:
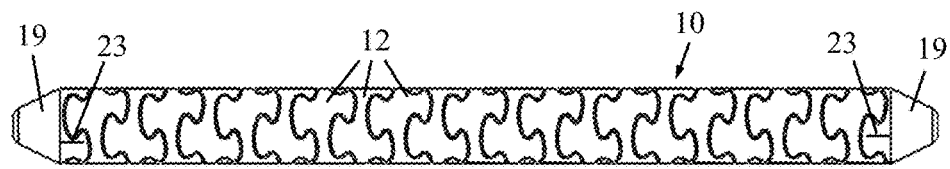
FIG. 7 is a simplified illustration of one pattern of link members for the fusion rod.

Reference is now made to FIG. 7, which illustrates a straight orientation of the link members 12 of rod 10. In this embodiment, the link members are interlocked with each other over the full length of rod 10. Rod 10 has tapered or chamfered ends 19. In all embodiments of the invention, rod 10 may have one or more markers 23 for orienting the rod 10 within the tulip of the pedicle screw at a desired orientation.

Figure 8:
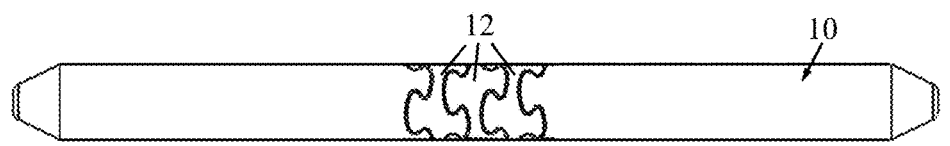
FIG. 8 is a simplified illustration of another pattern of link members for the fusion rod.

Reference is now made to FIG. 8, which illustrates another version of the rod in a straight orientation, in which link members 12 extend only over a partial length of rod 10.

Figure 9:
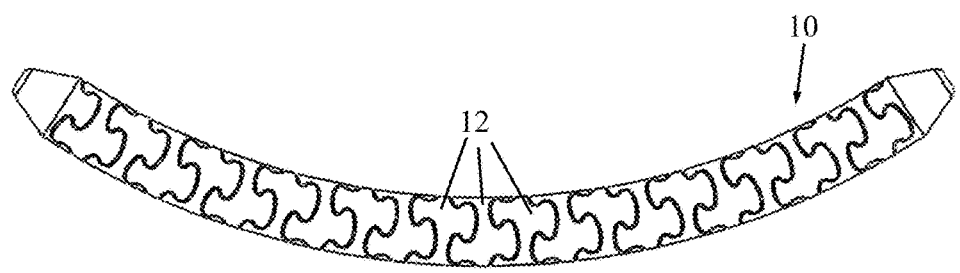
FIG. 9 is a simplified illustration of a curved orientation of the fusion rod, in accordance with a non-limiting embodiment of the present invention.

Reference is now made to FIG. 9, which illustrates link members 12 of the rod 10 of FIG. 7 in a curved, bent orientation.

Figure 10:
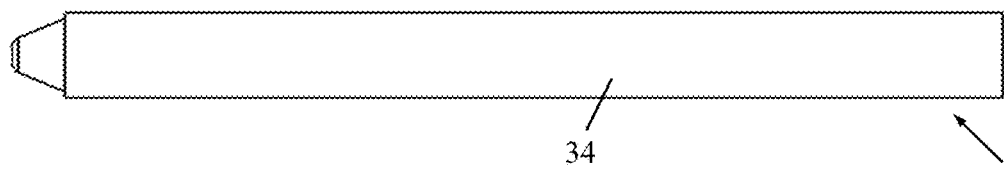
FIG. 10 is a simplified illustration of a cover (e.g., polymeric covering) for the fusion rod.

Reference is now made to FIG. 10, which illustrates a cover 34 (e.g., polymeric covering) for the fusion rod 10. Cover 34 may protect the rod from body fluids and protect body tissues from being snagged in the gaps between the link members.

Figure 11:
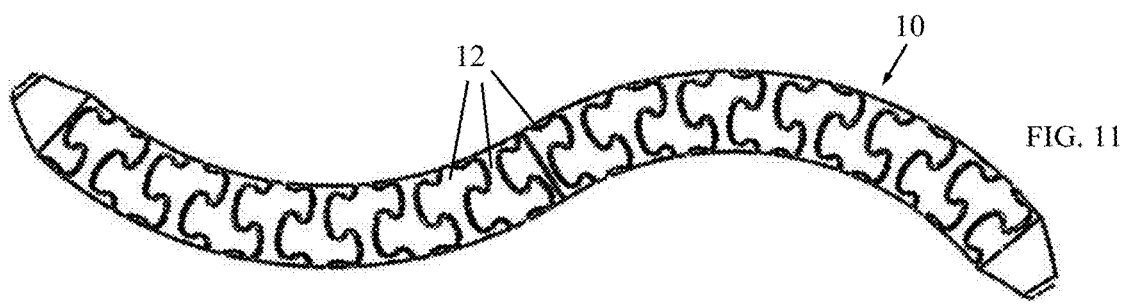
FIG. 11 is a simplified illustration of a double-curved orientation of the fusion rod, in accordance with a non-limiting embodiment of the present invention.

Reference is now made to FIG. 11, which illustrates a double-curved orientation of the fusion rod 10. The types of curved shapes available with the present invention are virtually limitless.

Figure 12:
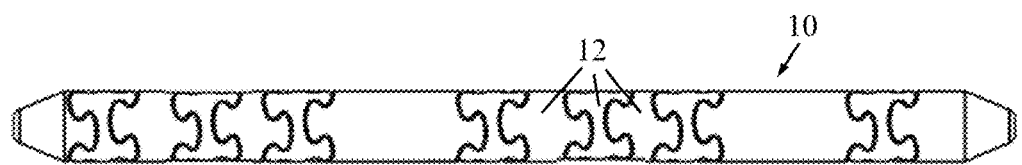
FIG. 12 is a simplified illustration of an irregular or non-repeating pattern of link members for the fusion rod.

Reference is now made to FIG. 12, which illustrates an irregular or non-repeating pattern of link members 12 for the fusion rod 10. Any pattern is possible and the type of pattern determines the bending shape of the rod.

Reference is now made to FIGS. 13-16, which illustrate a locking mechanism 40 for locking the flexible spinal fusion rod 10. The locking mechanism 40 may include, without limitation, a flexible elongate member 42 that passes through the lumens 14 of the link members 12 from one portion to another portion of the rod 10. For example, the flexible elongate member 42 may extend from one end of the rod to an opposite end of the rod to lock the entire length of the rod in a desired orientation. Alternatively, flexible elongate member 42 may extend from one portion of the rod not at the end to another portion (again not necessarily at the opposite end of the rod) to lock only a partial length of the rod in a desired orientation and leave the rest of the rod for flexing.

As with rod 10, the flexible elongate member 42 may be made of a surgically safe material, such as but not limited to, cobalt-chromium alloys, stainless steel alloys, titanium alloys or polymers, or an elastic material, such as a super-elastic material (e.g., nitinol). The flexible elongate member 42 may have a stopper 44 at one or both ends thereof. The locking mechanism 40 may further include a fastener 46 (FIGS. 14 and 15), such as but not limited to, a set screw, which presses the flexible elongate member 42 against the inner wall of the lumen 14 to lock the flexible elongate member 42 in place after it has been inserted through the lumens 14 from one end to another. The fastener 46 may be located in the chamfered end 19 or other locations in rod 10.

Figure 13:
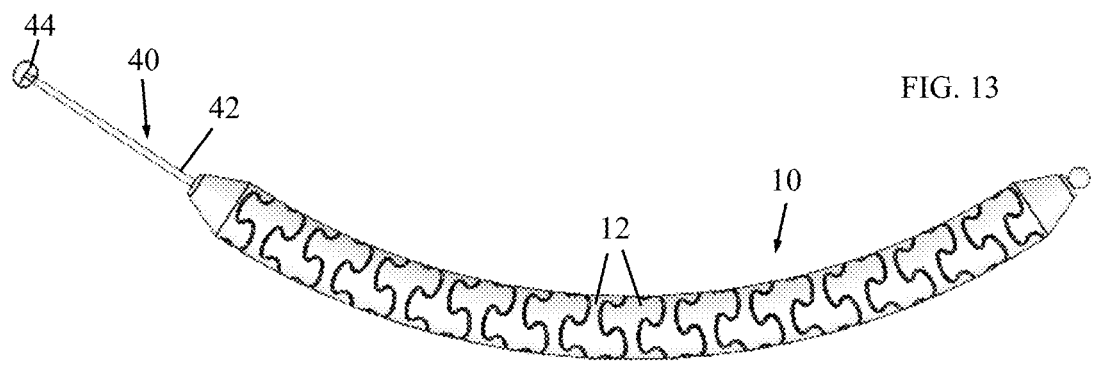
FIG. 13 is a simplified illustration of a locking mechanism for locking the flexible spinal fusion rod in one orientation (single curved orientation)
Figure 14:
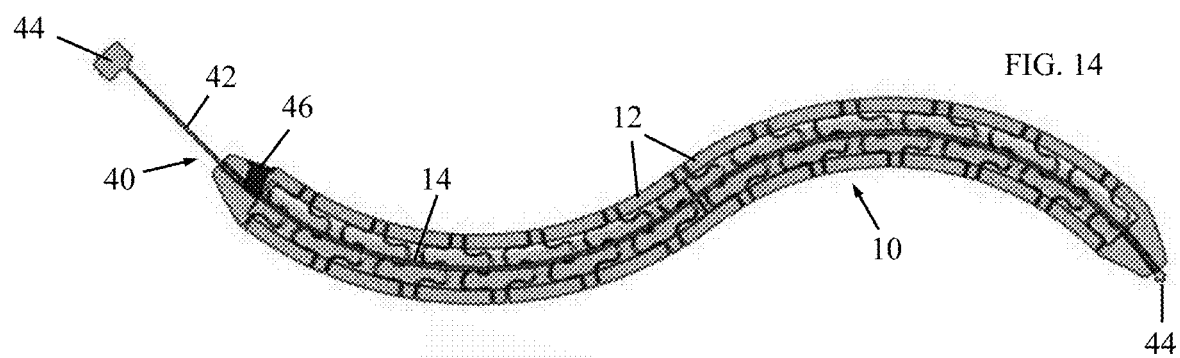
FIG. 14 is a simplified cutaway illustration of the locking mechanism.
Figure 15:
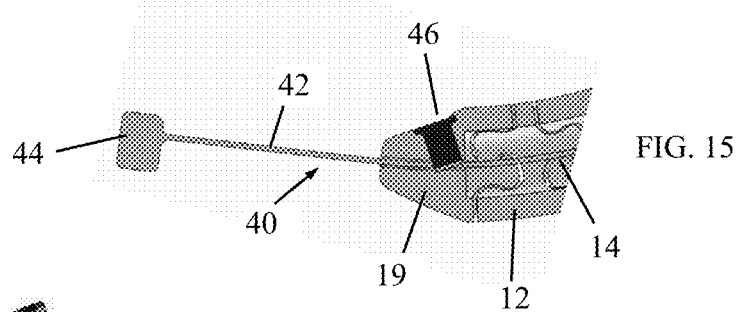
FIG. 15 is an enlarged illustration of a portion of the locking mechanism.
Figure 16:
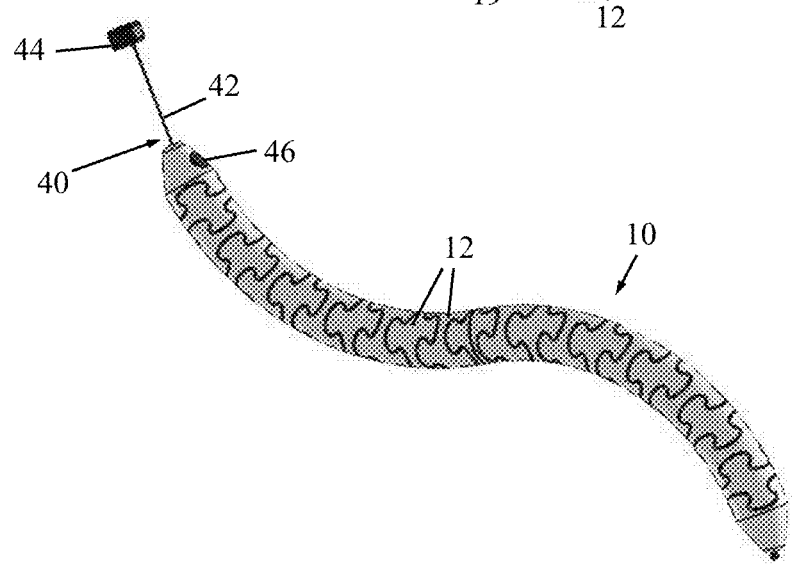
FIG. 16 is a simplified illustration of the locking mechanism for locking the flexible spinal fusion rod in another orientation (double-curved orientation).

In FIG. 13, locking mechanism 40 locks fusion rod 10 in a single curved orientation. In FIG. 16, locking mechanism 40 locks fusion rod 10 in a double-curved orientation.

Other locking mechanisms may be used, such as but not limited to, ratchets, pawls, detents and others.

What is claimed is:
1. A spinal rod assembly comprising:
a flexible spinal fusion rod comprising link members that articulate with one another so that said rod is formable into a curved orientation; and
a locking mechanism coupled to said link members and configured to lock said link members so that said rod is maintained in the curved orientation,
wherein said locking mechanism comprises a flexible elongate member that passes through lumens of said link members from one end to another end of said rod, and a fastener arranged to press said flexible elongate member against an inner wall of at least one of said lumens to lock said flexible elongate member in place, and wherein said flexible elongate member comprises a first stopper at a first end thereof and a second stopper at a second end thereof, opposite to said first end, and wherein said first and second stoppers each comprise an enlarged member sized to be incapable of entering said lumens of said link members.

2. The spinal rod assembly according to claim 1, wherein said first and second stoppers are not equal in size.

3. The spinal rod assembly according to claim 1, wherein said rod comprises at least one chamfered end.

4. The spinal rod assembly according to claim 1, wherein each of said link members comprises a male tenon that protrudes from a body portion and which is received in a female mortise of an adjacent link member.

5. The spinal rod assembly according to claim 4, wherein said male tenon comprises a distal convex portion which extends laterally on opposite sides of a longitudinal axis of said rod to lateral convex portions, and said male tenon tapers proximally from each of said lateral convex portions to inflection points located on opposite sides of said longitudinal axis, and said male tenon gradually narrows to a narrowest point on a concave path on opposite sides of said longitudinal axis and said male tenon gradually widens in a concave shape to said body portion, and said female mortise is shaped to complement shapes of said distal convex portion, said lateral convex portions, said concave path and said concave shape of said male tenon.

6. The spinal rod assembly according to claim 5, wherein a gap is between an outer edge of each of said lateral convex portions and an adjacent inner wall of each of said female mortises.

7. The spinal rod assembly according to claim 1, wherein said rod comprises one or more markers.

8. The spinal rod assembly according to claim 1, wherein said rod comprises a cover.

* * * * *